(12) United States Patent
Nelson

(10) Patent No.: US 6,821,529 B2
(45) Date of Patent: Nov. 23, 2004

(54) OLIGO(ETHYLENE GLYCOLL)-TERMINATED 1,2-DITHIOLANES AND THEIR CONJUGATES USEFUL FOR PREPARING SELF-ASSEMBLED MONOLAYERS

(76) Inventor: Deanna Jean Nelson, 104 Tasman Ct., Cary, NC (US) 27513

( * ) Notice: Subject to any disclaimer, the term of this patent is extended or adjusted under 35 U.S.C. 154(b) by 0 days.

(21) Appl. No.: 09/946,023

(22) Filed: Sep. 5, 2001

(65) Prior Publication Data

US 2003/0059865 A1 Mar. 27, 2003

(51) Int. Cl.[7] .................... A61K 38/00; C12N 11/08; G01N 33/545; C07K 18/08; C07K 17/14
(52) U.S. Cl. .................. 424/450; 424/94.1; 435/176; 435/180; 436/525; 436/531; 514/2; 530/402; 530/811; 530/815
(58) Field of Search ................. 435/174, 176, 435/177, 180; 530/402, 810, 811, 812, 815; 436/518, 524, 531, 525; 424/450, 74.1; 514/2

(56) References Cited

U.S. PATENT DOCUMENTS 6,277,489 B1 * 8/2001 Abbott et al. ............... 428/403
6,436,699 B1   8/2002 Berggren

FOREIGN PATENT DOCUMENTS

WO    WO99/14596    3/1999

OTHER PUBLICATIONS

M.Dijksma, et al. Formation and electrochemical characterization of self–assembled monolayers of thioctic acid on polycrystalline gold electrodes in phosphate buffer pH 7.4. Langmuir 2000, 16, 3852–3857.

C. Pale–Grosdemange, et al. Formation of self–assembled monolayers by chemisorption of derivatives of oligo(ethylene glycol) of structure $HS(CH_2)_{11}(OCH_2CH_2)_mOH$ on gold. J. Am. Chem. Soc. 1991, 113, 12–20.

S. Svedhem, et al. Synthesis of a series of oligo(ethylene glycol)–terminated alkanethiol amides designed to address structure and stability of biosensing interfaces. J. Org. Chem. 2001, 66 (No. 13), 4494–4503.

T. Carofiglio, et al. Synthesis, characterization, and chemisorption on gold of a β–cyclodextrin–lipoic acid conjugate. Tetrahedron Letters 2001, 42, 5241–5244.

K. Bandyopadhyay, et al. Self–assembled monolayers of bis–thioctic ester derivatives of oligoethyleneglycols: remarkable selectivity for K+/Na+ recognition. Chem. Commun. 2000, 141–142.

* cited by examiner

*Primary Examiner*—David M. Naff

(57) ABSTRACT

The present invention provides biotechnologically useful oligo(ethylene glycol)-terminated 1,2-dithiolane compositions and conjugates of these compositions with biological or non-biological receptor, ligand, sequestering, or reporter moieties. The invention also provides methods for the preparation of these compositions. Further, the invention provides self-assembled monolayer (SAM) compositions on a metal and methods for their preparation.

29 Claims, 1 Drawing Sheet

OLIGO(ETHYLENE GLYCOLL)-TERMINATED 1,2-DITHIOLANES AND THEIR CONJUGATES USEFUL FOR PREPARING SELF-ASSEMBLED MONOLAYERS

CROSS-REFERENCE TO RELATED APPLICATIONS

None.

STATEMENT REGARDING FEDERALLY SPONSORED RESEARCH & DEVELOPMENT

No Federally sponsored research and development was used in making this invention.

BACKGROUND OF THE INVENTION

Since they were first reported by Nuzzo and Allara in 1983, self-assembled monolayers (SAMs) composed of sulfur-terminated organic molecules adsorbed on and adherent to gold surfaces have shown broad utility in lubrication, electrochemistry, electronic and vibrational spectroscopy, photochemistry, diagnostics, the modification of biochemical membranes, catalysis, drug delivery, and facile modification of the absorptive properties of surfaces. (R. G. Nuzzo and D. L. Allara. Adsorption of bifunctional organic disulfides on gold surfaces. J. Am. Chem. Soc. 1983; 105: 4481–4483.) More recently, organic modifications of gold surfaces by SAMs have proven to be successful in nano-technological biosensor applications, e.g., in commercially available chips for biomolecular interaction analysis with surface plasmon resonance. (S. Löfås, B. Johnsson, K. Tegendahl, and I. Rönnberg. Colloids Surf. B 1993; 1: 83–89.)

For example, Dijksma and coworkers have reported that an electrochemical immunosensor composed of self-assembled monolayers of cysteine or N-acetylcysteine on gold electrodes is useful for the detection of interferon-γ at the attomolar level. (M. Dijksma, B. Kamp, J. C. Hoogvliet, and W. P. van Bennekom. Development of an electrochemical immunosensor for direct detection of interferon-γ at the attomolar level. Analyt. Chem. 2001; 73: 901–907.) Similarly, Darder and coworkers have found that horseradish peroxidase retained its activity when immobilized onto a gold surface via a 3-thiopropionate tether and was useful as a peroxide biosensor. (M. Darder, K. Takeda, F. Pariente, E. Lorenzo, and H. D. Abruña. Dithiobissuccinimidyl propionate as an anchor for assembling peroxidases at electrodes surfaces and its application in a $H_2O_2$ biosensor. Analyt. Chem. 1999; 71: 5530–5537.)

Likewise, poly- and oligo(ethylene glycols) (PEGs or OEGs, respectively; Structure 1, where $R_1$ is MeO or HO and $R_2$ is OH) have found widespread use in a variety of biotechnological and commercial applications, including the preparation of surfactants, ion-conducting materials, and conjugates of low and high molecular weight molecules. Investigators have found that these glycols provide good anchors for biological and non-biological receptor/reporter molecules or for ligands for biological and non-biological chelation or binding sites. Moreover, both PEGs and OEGs are known to reduce the nonspecific binding of proteins and other bioactive molecules to the surface to which they are conjugated. PEG and OEG derivatives are ideal for these applications because they are inexpensive, water soluble, stable, nonantigenic and non-immunogenic, and commercially available in a wide range of molecular weight distributions.

$R_1$—$CH_2CH_2O$—$(CH_2CH_2O)_x$—$CH_2CH_2$—$R_2$    Structure 1

In addition, conjugation with more highly branched and dendritic poly- and oligo(ethylene glycols) has been reported to be useful for improving the stability of protein drugs. [(a) D. C. Tully and J. M. J. Frechet. Dendrimers at surfaces and interfaces: chemistry and applications. Chem. Commun. 2001; 1229–1239. (b) I. Fuke, T. Hayashi, Y. Tabata, and Y. Ikada. Synthesis of poly(ethylene glycol) derivatives with different branchings and their use for protein modification. J. Controlled Release 1994; 30: 27–34. (c) J. M. Harris, F. M. Veronese, P. Caliceti, and O. Schiavon, U.S. Pat. No. 5,932,462.]

The broad utility of both classes of reagents (i.e., SAMs and PEGS or OEGS) suggests that synergistic benefits would obtain if libraries of reagents were available that combined the beneficial attributes of a SAM with those a PEG or OEG and exhibited additional features, such as the presence of reactive or activated groups at one end of each PEG or OEG chain. This combination of attributes would enable attachment of one terminus of such a combined SAM-forming-OEG reagent to a metal surface, yielding a SAM-OEG reagent, and attachment of a biological or non-biological receptor, ligand or reporter moiety at each of the other activated or reactive termini of the combined SAM/OEG reagent. The literature reports that describe examples of combined SAM/OEG reagents are limited to disclosures of methods of synthesis of OEG conjugates of linear alkyl monothiols and the effects of structure on the stability and physico-chemical properties of the reagents and the SAMs formed from them. (S. Svedhem, C-A. Hollander, J. Shi, P. Konradsson, B. Liedberg, and S. C. T. Svensson. Synthesis of a series of oligo(ethylene glycol)-terminated alkanethiol amides designed to address structure and stability of biosensing surfaces. J. Org. Chem. 2001; 66: 4494–4503.) Thus, the known reagents are limited to alkyl monothiols that lack an activated or reactive terminus at the end of the OEG chain and other desirable attributes that would enhance their utility.

Clearly, significant biotechnological advances in a spectrum of areas would be possible if activated or reactive, oligo(ethylene glycol)-terminated reagents and OEG-terminated reagents conjugated with a biological or non-biological receptor, ligand or reporter moiety useful for preparing self-assembled monolayers on gold were available. The present invention addresses this need.

SUMMARY OF THE INVENTION

The invention is based upon the recognition that the availability of activated or reactive, oligo(ethylene glycol)-terminated dithiolane compositions suitable for use in preparing self-assembled monolayers on a metal would enable significant advances in the biotechnological arts.

Thus, the invention provides highly versatile tethers suitable for immobilization on a metal backbone, wherein one segment of the tether is a linear or branched oligo(ethylene glycol) residue and the other segment of the tether is an alkyl-substituted 1,2-dithiolane. Further, one terminus of each oligo(ethylene glycol) residue is activated or reactive, enabling the preparation of conjugates of the oligo(ethylene glycol)-terminated dithiolane compositions that are also suitable for immobilization on a metal backbone.

One embodiment of the present invention comprises linear or branched oligo(ethylene glycol)-terminated 3-alkyl-1,2-dithiolanes having the formula:

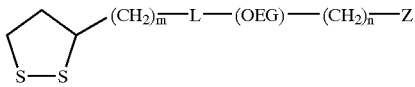

wherein m is from about 3 to about 20; n is from 2 to about 6; OEG is shorthand for a linear oligoether having the general structure —(CH$_2$CH$_2$O)$_x$— wherein x is from 2 to about 100, or for a branched oligoether wherein each branch comprises a linear oligoether having this general structure; one terminus of the OEG residue is covalently joined to the terminus of the alkyl side chain of the dithiolane by a linker L, wherein L is N, O, S, P, or an amide or hydrazide group; and each of the other termini of the OEG residue is a reactive or activated substituent Z that can be joined covalently to a biological or non-biological, ligand, sequestering, or reporter moiety. Examples of suitable reactive or activated substituents Z include an amino, guanidino, sulfhydryl, or activated ester moiety; a substituent that is reactive toward nucleophilic displacement, such as chloride, bromide, iodide, tosylate, tresylate, or mesylate; a group that is reactive toward nucleophilic addition, such as cyanate, isocyanate, thiocyanate, isothiocyanate, maleimide, oxirane, thiirane, or azirane; a carbonyl group; or a hydroxyl group.

A preferred embodiment comprises oligo(ethylene glycol)-terminated thioctic acid derivatives having the formula:

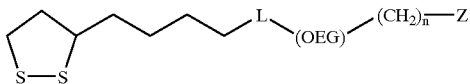

wherein n is from 2 to about 6; the symbol OEG is a linear oligoether having the general structure —(OCH$_2$CH$_2$)$_x$— and x is from 2 to about 100, or is a branched oligoether wherein each branch comprises a linear oligoether having this general structure; one terminus of the OEG residue is covalently joined to the alkyl side chain of thioctic acid by a linker L, wherein L is amide or hydrazide; and each of the other termini of the OEG residue is a reactive or activated substituent Z that can be joined covalently to a biological or non-biological ligand or reporter moiety.

A particularly preferred embodiment comprises oligo (ethylene glycol)-terminated d-thioctic acid derivatives having the formula:

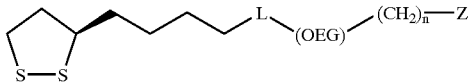

wherein n is from 2 to about 6; the symbol OEG is a linear oligoether having the structure —(OCH$_2$CH$_2$)$_x$— and x is from 2 to about 100, or is a branched oligoether wherein each branch comprises a linear oligoether having this structure; one terminus of the OEG residue is covalently joined to the alkyl side chain of d-thioctic acid by a linker L, wherein L is amide or hydrazide; and each of the other termini of the OEG residue is a reactive or activated substituent Z that can be joined covalently to a biological or non-biological ligand or reporter moiety.

Another embodiment of the present invention comprises oligo(ethylene glycol)-terminated 4-alkyl-1,2-dithiolanes having the formula:

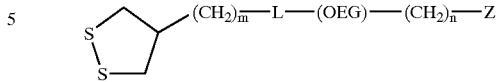

wherein m is from 3 to about 20; n is from 2 to about 6; the symbol OEG is a linear oligoether having the structure —(OCH$_2$CH$_2$)$_x$— and x is from 2 to about 100, or is a branched oligoether wherein each branch comprises a linear oligoether having this structure; one terminus of the OEG residue is covalently joined to the terminus of the alkyl side chain of the dithiolane by a linker L, wherein L is N, O, S, P, or an amide, or hydrazide; and each of the other termini of the OEG residue is a reactive or activated substituent Z that can be joined covalently to a biological or non-biological ligand or reporter moiety. Examples of suitable reactive or activated substituents Z include an amino, guanidino, sulfhydryl, or activated ester moiety; a substituent that is reactive toward nucleophilic displacement, such as chloride, bromide, iodide, tosylate, tresylate, or mesylate; a group that is reactive toward nucleophilic addition, such as cyanate, isocyanate, thiocyanate, isothiocyante, maleimide, oxirane, thiirane, or azirane; a carbonyl group; or a hydroxyl group.

Also provided in accordance with the invention are conjugates of these activated polymers with a biological or non-biological receptor, ligand, sequestering, or reporter moiety such as a polypeptide, protein, enzyme, phospholipid, lipid, liposome, nucleoside, oligonucleotide, drug, dye, antibody reporter molecule, ligand, cyclodextrin, carceplex, boronate, biological membrane, or a surface of a solid material that is compatible with living organisms, tissue, or fluids. Further provided are methods for preparation of these conjugates.

Also provided in accordance with the invention is a self-assembled monolayer (SAM) composition comprising an activated or reactive, OEG-modified-1,2-dithiolane composition or a conjugate of an OEG-modified-1,2-dithiolane composition adherent to gold, silver, copper, mercury, or an amalgam of these metals. A SAM composition comprising an activated or reactive, OEG-modified-1,2-dithiolane composition or a conjugate of an OEG-modified-1,2-dithiolane composition adherent to gold is most preferred. Further provided are methods for the preparation of these self-assembled monolayers and methods for their dissociation.

The unexpected utility of an activated or reactive, oligo (ethylene glycol)-terminated 1,2-dithiolane composition of the present invention or a conjugate of a reactive, OEG-terminated 1,2-dithiolane composition of the present invention as compared to the utility of the linear OEG-terminated, linear alkyl monothiols known in the art is believed to come from five sources. First, the 1,2-dithiolane segment of a 1,2-dithiolane composition of the present invention reacts with gold or another metal of the present invention to provide a self-assembled monolayer (SAM) composition that is stabilized by multiple sulfur-metal bonds. The multiple sulfur-metal bonds render the resulting SAM composition more stable than that of a monothiol. Second, the other segment of a 1,2-dithiolane composition of the present invention presents at least one activated or reactive terminus available for binding a biological or non-biological receptor, ligand, sequestering, or reporter moiety, or presents at least one terminus to which a biological or non-biological receptor, ligand, sequestering, or reporter moiety may be bound covalently. Third, when bound to the metal surface, a 1,2-dithiolane composition of the present invention is chemically stable in a wide variety of hostile media and conditions. This stability enables presentation of at least one biological or non-biological receptor, ligand or reporter moiety and capture and/or extraction and/or sequestering of a species of interest from a complex environment without undesirable dissociation of the oligo(ethylene glycol)-terminated dithiolane-metal complex during exposure to the hostile environment. Fourth, each of the opposing termini at the end of the OEG-portion of a 1,2-dithiolane composition of the present invention is reactive with, or may be activated to be reactive with, any one of a broad spectrum of electrophilic or nucleophilic reagents. This reactivity enables covalent attachment of a biological or non-biological receptor, ligand, sequestering, or reporter moiety to an activated or reactive, oligo(ethylene glycol)-terminated 1,2-dithiolane composition of the present invention either prior to its attachment to a metal or following its attachment to a metal. Further, if the OEG-portion of a 1,2-dithiolane composition of the present invention is branched, each activated or reactive terminus of an OEG-branch may be joined covalently to a biological or non-biological receptor, ligand or reporter moiety, thereby enabling presentation of a plurality of ligand or reporter moieties. Presentation of a plurality of a biological or non-biological receptor, ligand or reporter moieties is believed to enable more effective binding of a species of interest and its sequestration from a complex environment. Fifth, each composition of the present invention presents a moderately hydrophilic surface (i.e., the OEG-portion of a composition of the present invention) to the external environment. Monolayers of poly- or oligo(ethylene glycol) derivatives are known to minimize non-specific binding of biomolecules to the interactive terminus of the SAM. (C. Pale-Grosdemange, E. S. Simon, K. L. Prime, and G. M. Whitesides. Formation of self-assembled monolayers by chemisorption of derivatives of oligo(ethylene glycol) of structure $HS(CH_2)_{11}(OCH_2CH_2)_mOH$ on gold. J. Am. Chem. Soc. 1991; 113: 12–20.)

In addition to the five utilities cited above, a sixth utility has not been heretofore recognized by skilled artisans and applies particularly to the 1,2-dithiolane compositions of the present invention. Application of electrical voltage to a gold-sulfur-terminated reagent complex is known to effect the severance of the gold-sulfur reagent bond and release the reagent as a thiol. With respect to an OEG-terminated 1,2-dithiolane composition of the present invention, application of voltage to a gold-complex of a 1,2-dithiolane composition of the present invention severs both gold-sulfur bonds and releases the composition as the dithiol. Surprisingly, the inventor has found that this dithiol rapidly oxidizes to a ring-closed disulfide (i.e., a 1,2-dithiolane of the present invention).

This unexpected and rapid ring closure to a 1,2-dithiolane composition of the present invention offers distinct advantages to users of the present invention. One significant advantage relates to the relative nucleophilicity and reactivity of thiols compared to the nucleophilicity and reactivity of disulfides. Thiols are nucleophiles, and can undergo a variety of reactions, including, for example, the displacement of another thiol that is part of a disulfide. Thus, release of a thiol enables undesirable displacement reactions to occur, reactions that destroy (i.e., "scramble") existing disulfide bonds that may be critical to the structure and activity of a protein and cause its inactivation or denaturation. (Insulin is an example of a protein in which maintenance of the native disulfide bonds is critical. If insulin is exposed to a thiol, "scrambling" of the internal disulfide bonds takes place, and the protein is inactivated.) In contrast, after release from a SAM composition of the present invention, a 1,2-dithiolane of the present invention is re-formed. The disulfide (i.e., 1,2-dithiolane) thus formed is not a nucleophile and does not cause displacement reactions. The lack of chemical reactivity of the 1,2-dithiolane segment of a 1,2-dithiolane of the present invention is advantageous to the user of the present invention in a number of ways, including, by way of example, enabling monitoring of a 1,2-dithiolane composition of the present invention by surface plasmon resonance or mass spectrometry.

A seventh advantage of the 1,2-dithiolanes of the present invention relates specifically to the embodiments in which the 1,2-dithiolane is thioctic acid, d-thioctic acid or a derivative thereof. d-Thioctic acid is a natural substance found in mammals and is an important biological anti-oxidant and enzyme co-factor. Since some of the 1,2-dithiolanes of the present invention are derivatives of d-thioctic acid, it is reasonable to anticipate that these dithiolanes will be physiologically compatible. This is advantageous to the user of the present invention in a number of ways, including, by way of example, enabling use of such a 1,2-dithiolane of the present invention as a means for drug delivery.

DETAILED DESCRIPTION OF THE INVENTION

EXAMPLE 1

Figure 1:
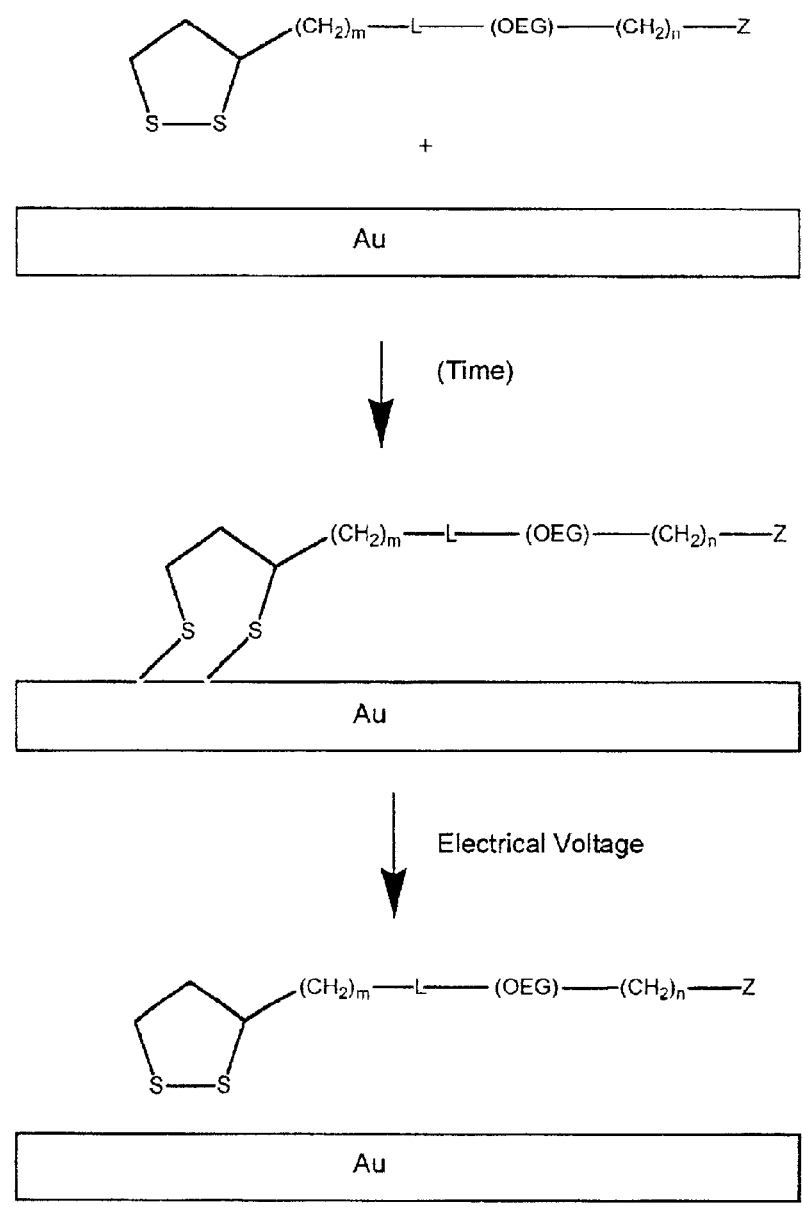
FIG. 1 is a cartoon of the manner in which a 1,2-dithiolane composition of the present invention reacts with a metal surface (e.g., gold) to provide a self-assembled monolayer (SAM) composition of the present invention and subsequently is released by the application of electrical voltage and nearly instantaneously oxidized to re-form the corresponding 1,2-dithiolane.

General Procedure for Coupling Thioctic Acid and an OEG-Amine.

To a solution of thioctic acid (0.15 mmol) in methylene chloride (4 mL) at 0° C. is added an OEG-amine (0.23 mmol), N-hydroxybenzotriazole (0.23 mmol) and finally N-(3-dimethylaminoproopyl)-N'-ethylcarbodiimide (EDC) (0.23 mmol). The reaction mixture is allowed to attain room temperature. After 12 h, it is diluted with methylene chloride (10 mL) and washed with 0.1 M HCl (10 mL) and water (10 mL). The organic solution is dried over anhydrous magnesium sulfate and evaporated. The crude product is crystallized or purified by flash chromatography (ethyl acetate/hexane or ethyl acetate/methanol).

(a) In this manner, thioctic acid is coupled with an OEG-amine having the general structure $H_2N-CH_2CH_2-(OCH_2CH_2)_x-NH-t-BOC$, where x is 2, 4, 6, 8, 10, and 12. The protecting t-BOC group is removed by treatment with trifluoroacetic acid to provide a reactive, oligo(ethylene glycol)-terminated thioctamide suitable for coupling (i.e., conjugating) with a biological or non-biological receptor, ligand or reporter moiety.

(b) Likewise, in this manner, thioctic acid is coupled with an OEG-amine having the general structure $H_2N-CH_2CH_2-(OCH_2CH_2)_x-CO_2H$, where x is 2, 4, 6, 8, 10, and 12, to provide a reactive, oligo(ethylene glycol)-terminated thioctamide suitable for coupling with a biological or non-biological receptor, ligand or reporter moiety.

(c) Likewise, in this manner, thioctic acid is coupled with an OEG-amine having the general structure $H_2N-CH_2CH_2-(OCH_2CH_2)_x-OH$, where x is 2, 4, 6, 8, 10, and 12, to provide a reactive, oligo(ethylene glycol)-terminated thioctamide suitable for coupling with a biological or non-biological receptor, ligand or reporter moiety.

(d) Thioctic acid is allowed to react with disuccinimyl carbonate in methylene chloride solution containing triethylamine to provide N-oxysuccinimidyl thioctate (NHS-thioctate), an activated ester of thioctic acid. Then NHS-thioctate is allowed to react with one equivalent of an OEG-hydrazine having the general structure $H_2N-NH-CH_2CH_2-(OCH_2CH_2)_x-NH$-t-BOC, where x is 2, 4, 6, 8, 10, and 12. The protecting t-BOC group is removed by treatment with trifluoroacetic acid to provide a reactive, oligo(ethylene glycol)-terminated thioctyl hydrazide suitable for coupling with a biological or non-biological receptor, ligand or reporter moiety.

EXAMPLE 2

General Procedure for Coupling d- or l-Thioctic Acid and an OEG-Amine.

Racemic thioctic acid is resolved into its d- and l-isomers.

(a) Using the general procedure described in Example 1, d-thioctic acid is coupled with an OEG-amine having the general structure $H_2N-CH_2CH_2-(OCH_2CH_2)_x-NH$-t-BOC, where x is 2, 4, 6, 8, 10, and 12. The protecting t-BOC group is removed by treatment with trifluoroacetic acid to provide a reactive, linear oligo(ethylene glycol)-terminated d-thioctamide suitable for coupling with a biological or non-biological receptor, ligand or reporter moiety.

(b) Likewise, in this manner, d-thioctic acid is coupled with an OEG-amine having the general structure $H_2N-CH_2CH_2-(OCH_2CH_2)_x-CO_2H$, where x is 2, 4, 6, 8, 10, and 12, to provide a reactive, oligo(ethylene glycol)-terminated d-thioctamide suitable for coupling with a biological or non-biological receptor, ligand or reporter moiety.

(c) Using the general procedure described in Example 1, d-thioctic acid is coupled with an OEG-amine having the general structure $H_2N-CH_2CH_2-(OCH_2CH_2)_x-OH$, where x is 2, 4, 6, 8, 10, and 12, to provide a reactive, oligo(ethylene glycol)-terminated d-thioctamide suitable for coupling with a biological or non-biological receptor, ligand or reporter moiety.

(d) Using the general procedure described in Example 1, l-thioctic acid is coupled with an OEG-amine having the general structure $H_2N-CH_2CH_2-(OCH_2CH_2)_x-NH$-t-BOC, where x is 2, 4, 6, 8, 10, and 12. The protecting T-BOC group is removed by treatment with trifluoroacetic acid to provide a reactive, oligo(ethylene glycol)-terminated l-thioctamide suitable for coupling with a biological or non-biological receptor, ligand or reporter moiety.

(e) Likewise, in this manner, l-thioctic acid is coupled with an OEG-amine having the general structure $H_2N-CH_2CH_2-(OCH_2CH_2)_x-CO_2H$, where x is 2, 4, 6, 8, 10, and 12, to provide a reactive, oligo(ethylene glycol)-terminated l-thioctamide suitable for coupling with a biological or non-biological receptor, ligand or reporter moiety.

(f) Likewise, in this manner, l-thioctic acid is coupled with an OEG-amine having the general structure $H_2N-CH_2CH_2-(OCH_2CH_2)_x-OH$, where x is 2, 4, 6, 8, 10, and 12, to provide a reactive, oligo(ethylene glycol)-terminated l-thioctamide suitable for coupling with a biological or non-biological receptor, ligand or reporter moiety.

EXAMPLE 3

General Procedure for Coupling Thioctyl Hydrazide and an OEG-Aldehyde.

To a solution of thioctyl hydrazide (0.15 mmol) in ethanol (5 mL) at 0° C. is added OEG-aldehyde (0.23 mmol) and sodium cyanoborohydride (0.5 mmol). The reaction mixture is stirred until thin-layer chromatographic analysis of an aliquot of the reaction mixture indicates that Schiff-base formation and reduction to the secondary amine are complete. The product is isolated by the addition of cold diethyl ether, washed with fresh ether, and purified by flash chromatography on silica gel.

EXAMPLE 4

General Procedure for Coupling Thioctyl Hydrazide and an OEG-Mesylate.

To a solution of thioctyl hydrazide (0.15 mmol) in ethanol (5 mL) at 0° C. is added OEG-Mesylate (0.23 mmol). The reaction mixture is stirred with gentle warming until thin-layer chromatographic analysis of an aliquot of the reaction mixture indicates that alkylation is complete. The product is isolated by the addition of cold diethyl ether, washed with fresh ether and purified by flash chromatography on silica gel.

EXAMPLE 5

General Method for the Preparation of a SAM Composition on Gold.

(a) A 1 mM solution of an OEG-terminated 1,2-dithiolane composition of the present invention is prepared in deoxygenated, absolute alcohol, and a gold surface is placed in contact with the solution for 24 hours at room temperature.

In the case of a conjugate of a 1,2-dithiolane of the present invention, it is preferred that the conjugate be prepared prior preparation of a SAM composition. This is accomplished by reacting a reactive or activated, OEG-terminated 1,2-dithiolane of the present invention with a biological or non-biological receptor, ligand, sequestering, or reporter moiety such as a polypeptide, protein, enzyme, phospholipid, lipid, liposome, nucleoside, oligonucleotide, drug, dye, antibody, reporter molecule, ligand, cyclodextrin, carceplex, boronate, biological membrane, or a surface of a solid material that is compatible with living organisms, tissue, or fluids. Alternatively, a biological or non-biological receptor, ligand, sequestering, or reporter moiety such as a polypeptide, protein, enzyme, phospholipid, lipid, liposome, nucleoside, or oligonucleotide; drug, dye, antibody, reporter molecule, ligand, cyclodextrin, carceplex, boronate, biological membrane, or a surface of a solid material that is compatible with living organisms, tissue, or fluids is covalently bound to a reactive or activated, OEG-terminated SAM composition of the present invention.

(b) A gold surface is exposed to a 50 mM solution of an OEG-terminated 1,2-dithiolane composition in 100 mM phosphate buffer, pH 7.4, at room temperature. Adsorption is achieved at open circuit or at an applied potential.

In the case of a conjugate of a 1,2-dithiolane composition of the present invention, it is preferred that the conjugate be prepared prior preparation of a SAM composition. This is accomplished by reacting a reactive or activated, OEG-terminated 1,2-dithiolane composition of the present invention with a biological or non-biological receptor, ligand, sequestering, or reporter moiety such as a polypeptide, protein, enzyme, phospholipid, lipid, liposome, nucleoside, oligonucleotide, drug, dye, antibody, reporter molecule, ligand, cyclodextrin, carceplex, biological membrane, or a surface of a solid material that is compatible with living organisms, tissue, or fluids. Alternatively, a biological or non-biological receptor, ligand, sequestering, or reporter moiety such as a polypeptide, protein, enzyme, phospholipid, lipid, liposome, nucleoside, or oligonucleotide; drug, dye, antibody, reporter molecule, ligand, cyclodextrin, carceplex, biological membrane, or a surface of a solid material that is compatible with living organisms, tissue, or fluids is covalently bound to the OEG-terminated SAM composition.

EXAMPLE 6

General Method for the Removal of a SAM Composition on Gold.

A SAM composition of the present invention is removed from the gold in 100 mM phosphate buffer, pH 7.4, by application of potential pulses for about 15 minutes in a buffer flow of about 0.5 mL/min.

EXAMPLE 7

Conjugation of an Carboxyl-OEG-terminated 1,2-Dithiolane with an Enzyme.

A carboxyl-OEG-terminated thioctamide (x is 8) is prepared as described in Example 1(b). The terminal carboxyl group of the OEG portion of the composition is converted to an activated, N-hydroxysuccinimidyl (NHS) ester by treatment with disuccinimidyl carbonate in methylene chloride solution to provide an activated ester of the OEG-terminated thioctamide. A solution of horseradish peroxidase (HRP) is prepared in 5 mM phosphate buffer, pH 7.0, at a concentration of about 1 mg/mL. An equimolar volume of the HRP solution is added to the NHS-ester of the OEG-terminated thioctamide and the resulting mixture is allowed to stir for 24 hours at 4° C.

EXAMPLE 8

Conjugation of a Hydroxy-OEG-terminated 1,2-Dithiolane with an Oligonucleotide Probe.

Thioctic acid is coupled with an OEG-amine having the structure $H_2N-CH_2CH_2-(OCH_2CH_2)_{10}-OH$ to provide a reactive oligo(ethylene glycol)-terminated thioctamide, thioctamide-$CH_2CH_2-(OCH_2CH_2)_{10}-OH$. This thioctamide is coupled with a phosphoramidite-protected oligo-dT sequence using standard phosphoramidite chemistry, and the product is hydrolyzed to provide thioctamide-$CH_2CH_2-(OCH_2CH_2)_{10}-O$-oligo-dT.

(b) Preparation of the thioctamide-$CH_2CH_2-(OCH_2CH_2)_{10}-O$-oligo-dT SAM.

A gold surface is prepared. The surface is exposed to a phosphate buffer solution of the thioctamide-$CH_2CH_2-(OCH_2CH_2)_{10}-O$-oligo-dT composition for 4 hours. Ellipsometric measurements result in values that are in good agreement with those expected for a well-packed SAM containing trans-extended alkanethiolates.

It is known that oligo-dT chains bind with the poly-A tails present on most mRNA sequences. Therefore, it is reasonable to anticipate that the oligo-dT-terminated SAM composition of the present invention will be useful for the isolation of mRNAs from complex media. Durst and colleagues (R. Durst et al. Analyt. Chem. 2001; 73: 3162–3167) have recently shown that the expression of mRNA can be used to distinguish living cells from dead ones.

EXAMPLE 9

(a) Conjugation of an Carboxyl-OEG-terminated 1,2-Dithiolane with a Polypeptide.

A carboxyl-OEG-terminated thioctamide (x is 8) is prepared as described in Example 1(b). The bis(1,1-dimethylethyl)ester of N-[(phenylmethoxy)carbonyl)glycyl-$N^5$[[[(3,4-dihydro-2,2,5,7,8-pentamethyl-2H-1-benzopyran-6-yl)sulfonyl]amino]iminomethyl]-L-omithylglycyl-L-aspartic acid (a protected RGD tripeptide) is prepared using the method of Roberts et al. (C. Roberts, C. S. Chen, M. Mrksich, V. Martichonok, D. E. Ingber, and G. M. Whitesides. J. Am. Chem. Soc. 1998; 120: 6548–6555.) The protecting phenylmethoxycarbonyl group is removed by hydrogenation over 10% Pd/C; the catalyst is removed by filtration and the crude amine is concentrated in vacuo. Equimolar quantities of the amine and the carboxyl-OEG-terminated thioctamide are combined, the flask is purged with nitrogen, dry DMF is added, and the stirred solution is cooled to 0° C. An excess of diphenylphosphoryl azide is added, followed by a solution of di-isopropyl ethylamine in DMF, and stirring at 0° C. is continued for 10 hours. The mixture is diluted with ethyl acetate and washed successively with water, 5% aqueous sodium bicarbonate, and brine. The organic phase is dried, and the solvent is removed in vacuo to give a residue that is chromatographed to give product. The remaining protective groups are removed by exposing a methylene chloride solution of the product to trifluoroacetic acid. Repeated precipitation of the product from methylene chloride using diethyl ether is used to purify the desired product, thioctamide-OEG-C(O)NH-GRGD-OH.

(b) Preparation of the thioctamide-OEG-C(O)NH-GRGD-OH SAM.

A gold surface is prepared. The surface is exposed to a phosphate buffer solution of the thioctamide-OEG-C(O)NH-GRGD-OH composition for 4 hours. Ellipsometric measurements result in values that are in good agreement with those expected for a well-packed SAM containing trans-extended alkanethiolates.

(c) Cell Attachment to the SAM.

The tripeptide arginine-glycine-aspartate (RGD) promotes cell adhesion by binding to cell surface integrin receptors. Bovine capillary endothelial cells are isolated from adrenal cortex and cultured. Cells are dissociated with trypsin-EDTA, washed with Dulbecco's Modified Eagle Medium containing 1% bovine serum albumin, and plated onto substrates in chemically defined media before incubation in 10% CO2 at 37° C. A fixed number of cells are plated onto substrates containing the thioctamide-OEG-C(O)NH-GRGD-OH-SAM composition. After 4 hours, substrates are gently washed in PBS and fixed with 4% paraformaldehyde in PBS for 30 min. The number of cells attached per field is determined from photographs taken of samples on a microscope at 200× magnification.

Alternatively, after incubation times ranging from 4 to 24 hours, the immobilized cells are not fixed with paraformaldehyde but are removed using two techniques. In some experiments, the SAM-bound cells are exposed to a solution containing soluble GRGDSP, a polypeptide that will detach the cells. In other experiments, a voltage is applied to the gold surface, and the gold-thiol bonds are severed, freeing the thioactamide-labeled cells.

EXAMPLE 10

Conjugation of an Amino-OEG-terminated 1,2-Dithiolane with a Sugar Phosphonate.

(a) Thioctic acid is coupled with an OEG-amine having the structure H$_2$N—CH$_2$CH$_2$—(OCH$_2$CH$_2$)$_x$—OH, where x is 10, to provide a reactive, oligo(ethylene glycol)-terminated thioctamide, thioctamide-CH$_2$CH$_2$—(OCH$_2$CH$_2$)$_{10}$—OH. This thioctamide is coupled with a protected mannose-6-phosphonate using standard phosphoramidite chemistry. Likewise, the oligo(ethylene glycol)-terminated thioctamide is coupled with a protected mannose-6-difluoromethylphosphonate using standard phosphoramidite chemistry. The protective groups are removed from each compound to provide thioctamide-CH$_2$CH$_2$—(OCH$_2$CH$_2$)$_{10}$—O-(6-methylphosphono)mannose and thioctamide-CH$_2$CH$_2$—(OCH$_2$CH$_2$)$_{10}$—O-(6-difluoromethylphosphono)mannose, respectively.

(b) Preparation of the thioctamide-CH$_2$CH$_2$—(OCH$_2$CH$_2$)$_{10}$—O-(6-methylphosphono)mannose SAM.

A gold surface is prepared. The surface is exposed to a phosphate buffer solution of the thioctamide-CH$_2$CH$_2$—(OCH$_2$CH$_2$)$_{10}$—O-(6-phosphonomethyl)mannose composition for 4 hours. Ellipsometric measurements result in values that are in good agreement with those expected for a well-packed SAM containing trans-extended alkanethiolates.

(c) Cell Attachment to the SAM.

The population of mannose-6-phosphate receptors is increased abnormally in breast cancer cells. Since mannose-6-phosphate is readily hydrolyzed, it is not useful as a ligand for selective extraction of cancer cells from media containing a variety of cell types. In contrast, mannose-6-phosphonate and mannose-6-difluoromethylphosphonate are stable to hydrolysis and retain the ability to bind to mannose-6-phosphate receptors.

The phosphonomannose-terminated SAM prepared as described in Example 10(b) is exposed to a serum sample containing breast cancer cells. After 4 hours, substrates are gently washed in PBS and fixed with 4% paraformaldehyde in PBS for 30 min. The number of cells attached per field is determined from photographs taken of samples on a microscope at 200× magnification. The number of cells attached per field demonstrates the utility of the SAM for selective extraction of cancer cells from complex environments.

EXAMPLE 11

Conjugation of a Hydroxyl-OEG-terminated 1,2-Dithiolane with a Drug (5-Aminosalicylic Acid).

Thioctic acid is coupled with an OEG-amine having the structure H$_2$N—CH$_2$CH$_2$—(OCH$_2$CH$_2$)$_{10}$—OH to provide a reactive oligo(ethylene glycol)-terminated thioctamide, thioctamide-CH$_2$CH$_2$—(OCH$_2$CH$_2$)$_{10}$—OH. This product is converted to the mesylate ester by reaction with methanesulfonyl chloride in methylene chloride solution containing triethylamine. The mesylate ester is isolated and purified by flash chromatography on silica gel.

5-Aminosalicylic acid is a drug used in the treatment of ulcerative colitis. To a solution containing an excess of 5-aminosalicylic acid hydrochloride and thioctamide-CH$_2$CH$_2$—(OCH$_2$CH$_2$)$_{10}$—O-Ms (the mesylate ester) in DMF is added triethylamine until dissolution of 5-aminosalicylic acid is achieved. The reaction is allowed to stir until thin-layer chromatographic analysis of an aliquot indicates reaction is complete. The 5-aminosalicylate conjugate is isolated and purified by flash chromatography on silica gel.

(b) Preparation of the thioctamide-CH$_2$CH$_2$—(OCH$_2$CH$_2$)$_{10}$-5-aminosalicylate SAM.

A gold surface is prepared. The surface is exposed to an ethanol solution of the thioctamide-CH$_2$CH$_2$—(OCH$_2$CH$_2$)$_{10}$-5-aminosalicylate composition for 4 hours. Ellipsometric measurements result in values that are in good agreement with those expected for a well-packed SAM containing trans-extended alkanethiolates.

The skilled artisan will appreciate that the invention has a number of advantages over the prior art, including the following. First, the availability of the compositions of the present invention enables the skilled artisan to use any of a broad spectrum of known chemistries to attach a specific, biological or non-biological receptor, ligand, sequestering, or reporter moiety of interest to the artisan to an activated or reactive, OEG-terminated 1,2-dithiolane composition of the present invention to provide a conjugate of the OEG-terminated 1,2-dithiolane composition. Second, the resulting conjugate is easily used, either as the pure component or as part of a mixture with other thiols, to prepare a stable, self-assembled monolayer composition of the present invention on gold, silver, copper, mercury, or an amalgam of these metals. Third, after use (e.g., for capture, sequestration, and extraction of a species of interest), dissociation of the SAM composition of the present invention is effected, not through the use of the harsh and non-specific chaotropic agents known in the art, but by the controlled application of electrical voltage to the SAM composition. Fourth, after dissociation, the dithiol that is released from the metal surface nearly instantaneously oxidizes to the ring-closed 1,2-dithiolane, providing a moiety that may be identified and quantitated using instrumental techniques such as surface plasmon resonance or mass spectrometry. Fifth, some embodiments of the 1,2-dithiolane compositions of the present invention are derivatives of a natural substance, d-thioctic acid. It is reasonable to anticipate that these embodiments, together with embodiments of the present invention that are derivatives of thioctic acid, will be compatible with physiological systems and will be useful for drug delivery, among other utilities.

The invention has been described with respect to several particular examples and embodiments. However, the foregoing examples and descriptions are not intended to limit the invention to the exemplified embodiments. The skilled artisan should recognize that variations can be made within the scope and spirit of the invention as described in the foregoing specification. The invention encompasses all alternatives, modifications, and equivalents that may be included within the true scope and spirit of the invention as defined by the appended claims.

I claim:

1. An oligo(ethylene glycol)-terminated 3-alkyl-1,2-dithiolane composition having the formula:

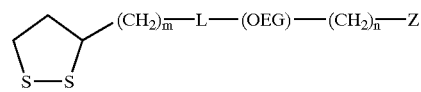

wherein m is 4; n is from 2 to about 6; OEG is a linear oligoether having the structure —(CH$_2$CH$_2$O)$_x$— wherein x is from 2 to about 100; one terminus of the OEG is covalently joined to the terminus of the 3-alkyl side chain of the dithiolane by a linker L, wherein is N, O, S, P, an amide or hydrazide; and another terminus of the OEG is a substituent Z, wherein Z is an amino group, carboxyl group, guanidino group, sulfhydryl group, an activated ester, a group that is reactive toward a nucleophilic group, or a carbonyl group.

2. An oligo(ethylene glycol)-terrrlinated 3-alkyl-1,2-dithiolane composition having the formula:

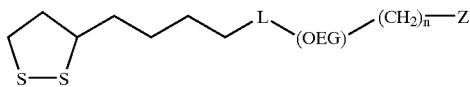

wherein n is from 2 to about 6; the 3-alkyl-1,2-dithiolane is d-thioctic acid or l-thioctic acid; OEG is a linear oligoether having the general structure —(OCH$_2$CH$_2$)$_x$— and x is from 2 to about 100; one terminus of the OEG is covalently joined to the terminus of the 3-alkyl side chain of the 1,2-dithiolane by a linker L, wherein L is N, O, S, P, an amide or hydrazide; and other terminus of the OEG is a substituent Z, wherein Z is an amino group, carboxyl group, guanidino group, sulfhydryl group, an activated ester, a group that is reactive toward a nucleophilic group, or a carbonyl group.

3. An oligo(ethylene glycol)-terminated 3-alkyl-1,2-dithiolane composition having the formula:

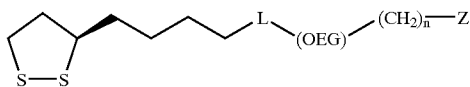

wherein n is from 2 to about 6; the 3-alkyl-1,2-dithiolane is d-thioctic acid OEG is a linear oligoether having the general structure —(OCH$_2$CH$_2$)$_x$— and x is from 2 to about 100; one terminus of the OEG is covalently joined to the terminus of the 3-alkyl side chain of the 1,2-dithiolane by a linker L, wherein L is N, O, S, P, an amide or hydrazide; and another terminus of the OEG is a substituent Z, wherein Z is an amino group, carboxyl group, guanidino group, sulfhydryl group, an activated ester, a group that is reactive toward a nucleophilic group, or a carbonyl group.

4. An oligo(ethylene glycol)-terminated 3-alkyl-1,2-dithiolane composition having the formula:

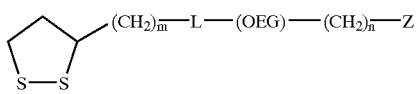

wherein m is 4; n is from 2 to about 6; OEG is a branched oligoether wherein each branch of the branched oligoether comprises a linear polyether having the general structure —(CH$_2$CH$_2$O)$_x$— wherein x is independently from 2 to about 100; one terminus of the branched oligoether is covalently joined to the terminus of the 3-alkyl side chain of the dithiolane by linker L, wherein L is N, O, S, P, an amide or hydrazide; and another terminus of each branch of the branched oligoether is a substituent Z, wherein Z is an amino group, carboxyl group, guanidino group, sulfhydryl group, an activated ester, a group that is reactive toward a nucleophilic group, or a carbonyl group.

5. An oligo(ethylene glycol)-terminated 3-alkyl-1,2-dithiolane composition having the formula:

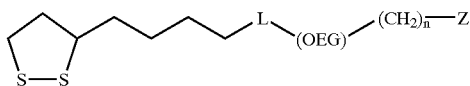

wherein n is from 2 to about 6; the 3-alkyl-1,2-dithiolane is d-thioctic acid or l-thioctic acid; OEG is a branched oligoether wherein each branch of the branched oligoether comprises a linear polyether having the general structure —(OCH$_2$CH$_2$)$_x$— wherein x is indepe dently from 2 to about 100; one terminus of the branched oligoether is covalently joined to the terminus of the 3-alkyl side chain of the 1,2-dithiolane by a linker L, wherein L is N, O, S, P, an amide or hydrazide; and another terminus of each branch of the branched oligoether is a substituent Z, wherein Z is an amino group, carboxyl group, guanidino group, sulfhydryl group, activated ester, a group that is reactive toward a nucleophilic group, or a carbonyl group.

6. An oligo(ethylene glycol)-terminated 3-alkyl-1,2-dithiolane composition having the formula:

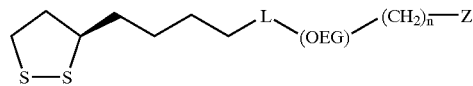

wherein n is from 2 to about 6; the 3-alkyl-1,2-dithiolane is d-thioctic acid; OEG is a branched oligoether wherein each branch of the branched oligoether comprises a linear polyether having the general structure —(OCH$_2$CH$_2$)$_x$— wherein x is independently from 2 about 100; one terminus of the branched oligoether is covalently joined to the terminus of th 3-alkyl side chain of the 1,2-dithiolane by a linker L, wherein L is N, O, S, P, an amide or hydrazide; and another terminus of the each branch of the branched oligoether is a substituent Z, wherein Z is an amino group, carboxyl group, guanidino group, sulfhydryl group, an activated ester, a group that is reactive toward a nucleophilic group, or a carbonyl group.

7. An oligo(ethylene glycol)-terminated 3-alkyl-1,2-dithiolane composition having the formula:

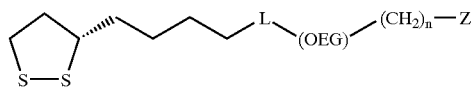

wherein n is from 2 to about 6; the 3-alkyl-1,2-dithiolane is l-thioctic acid OEG is a linear oligoether having the general structure —(OCH$_2$CH$_2$)$_x$— and x is from 2 to about 100; one terminus of the OEG is covalently joined to the terminus of the 3-alkyl side chain of the 1,2-dithiolane by a linker L, wherein L is N, O, S, P, an amide or hydrazide; and nother terminus of the OEG is a substituent Z, wherein Z is an amino group, carboxyl group, guanidino group, sulfhydryl group, an activated ester, a group that is reactive toward a nucleophilic group, or a carbonyl group.

8. An oligo(ethylene glycol)-terminated 3-alkyl-1,2-dithiolane composition having the formula:

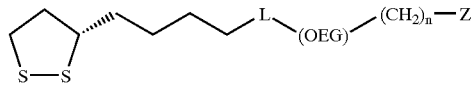

wherein n is from 2 to about 6; the 3-alkyl-1,2-dithiotane is l-thioctic acid; OEG is a branched oligoether wherein each branch of the branched oligoether comprises a linear polyether having the general structure —(OCH$_2$CH$_2$)$_x$— wherein x is independently from 2 t about 100; one terminus of the branched oligoether is covalently joined to the terminus of the 3-alkyl side chain of the 1,2-dithiolane by a linker L, wherein L is N, O, S, P, an amide or hydrazide; and another terminus of the each branch of the branched oligoether is a substituent Z, wherein Z is an amino group, carboxyl group, guanidino group, sulfhydryl group, an activated ester, a group that is reactive toward a nucleophilic group, or a carbonyl group.

9. A conjugate comprising an oligo(ethylene glycol)-terminated 3-alkyl-1,2-dithiolane composition having the formula:

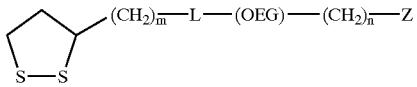

wherein m is 4; n is from 2 to about 6; OEG is a linear oligoether having the structure —(CH$_2$CH$_2$O)$_x$— wherein x is from 2 to about 100; one terminus of the OEG is covalently joined to the terminus of the 3-alkyl side chain of the dithiolane by a linker L, wherein is N, O, S, P, an amide or hydrazide; and another terminus of the OEG is a substituent Z, wherein Z is an activated ester or a group that is reactive toward a nucleophilic group; and a nucleophilic group conjugated to Z.

10. The conjugate of claim 9, wherein said nucleophilic group comprises a biologically active moiety.

11. The conjugate of claim 10, wherein said biologically active moiety is selected from the group consisting of enzymes, peptides, polypeptides, nucleotides, oligonucleotides, polynucleotides, immunoglobulins, antibodies, and lipids.

12. The conjugate of claim 9, wherein said nucleophilic group comprises a biological membrane.

13. The conjugate of claim 9, wherein said nucleophilic group comprises a reporter moiety.

14. The conjugate of claim 13, wherein said reporter moiety is selected from the group consisting of dyes, biotin, drugs, cyclodextrins, carceplexes, and boronates.

15. A conjugate comprising an oligo(ethylene glycol)-terminated 3-alkyl-1,2-dithiolane composition having the formula:

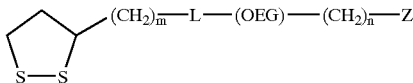

wherein m is 4; n is from 2 to about 6; OEG is a linear oligoether having the structure —(CH$_2$CH$_2$O)$_x$— wherein x is from 2 to about 100; one terminus of the OEG is covalently joined to the terminus of the 3-alkyl side chain of the dithiolane by a linker L, wherein is N, O, S, P, an amide or hydrazide; and another terminus of the OEG is a substituent Z, wherein Z is an amino group, guanidino group, sulfhydryl group, a group that is reactive toward an electrophilic group, a carbonyl group, or a hydroxyl group; and an electrophilic group conjugated to Z.

16. A conjugate comprising an oligo(ethylene glycol)-terminated 3-alkyl-1,2-dithiolane composition having the formula:

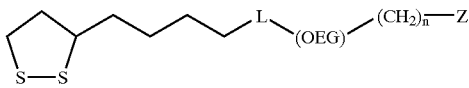

wherein n is from 2 to about 6; the 3-alkyl-1,2-dithiolane is d-thioctic acid or l-thioctic acid; OEG is a linear oligoether having the general structure —(OCH$_2$CH$_2$)$_x$— and x is from 2 to about 100; one terminus of the OEG is covalently joined to the terminus of the 3-alkyl side chain of the 1,2-dithiolane by a linker L, wherein L is N, O, S, P, an amide or hydrazide; and other terminus of the OEG is covalently joined to a substituent Z, wherein Z is a biologically active moiety, biological receptor, non-biological receptor, ligand, sequestering moiety, or reporter moiety.

17. A conjugate comprising an oligo(ethylene glycol)-terminated 3-alkyl-1,2-dithiolane composition having the formula:

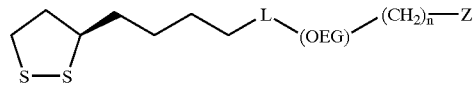

wherein n is from 2 to about 6; the 3-alkyl-1,2-dithiolane is d-thioctic acid OEG is a linear oligoether having the general structure —(OCH$_2$CH$_2$)$_x$— and x is from 2 to about 100; one terminus of the OEG is covalently joined to the terminus of the 3-alkyl side chain of the 1,2-dithiolane by a linker L, wherein L is N, O, S, P, an amide or hydrazide; and another terminus of the OEG is covalently joined to a substituent Z, wherein Z is a biologically active moiety, biological receptor, non-biological receptor, ligand, sequestering moiety, or reporter moiety.

18. A conjugate comprising an oligo(ethylene glycol)-terminated 3-alkyl-1,2-dithiolane composition having the formula:

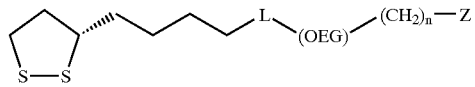

wherein n is from 2 to about 6; the 3-alkyl-1,2-dithiolane is l-thioctic acid OEG is a linear oligoether having the general structure —(OCH$_2$CH$_2$)$_x$— and x is from 2 t about 100; one terminus of the OEG is covalently joined to the terminus of the 3-alkyl side chain of the 1,2-dithiolane by a linker L, wherein L is N, O, S, P, an amide or hydrazide; and other terminus of the OEG is covalently joined to a substituent Z, wherein Z is a biologically active moiety, biological receptor, non-biological receptor, ligand, sequestering moiety, or reporter moiety.

19. A self-assembled monolayer composition comprising a conjugate comprising an oligo(ethylene glycol)-terminated 3-alkyl-1,2-dithiolane having the formula:

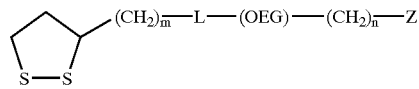

wherein m is 4; n is from 2 to about 6; OEG is a linear oligoether having the structure —(CH$_2$CH$_2$O)$_x$— wherein x is from 2 to about 100; one terminus of the OEG is covalently joined to the terminus of the 3-alkyl side chain of the dithiolane by a linker L, wherein is N, O, S, P, an amide or hydrazide; and another terminus of the OEG is a substituent Z, wherein Z is a biologically active moiety, biological receptor, non-biological receptor, ligand, sequestering moiety, or reporter moiety; and a metal selected from the group consisting of gold, silver, copper, mercury, and an amalgam of two or more of these metals conjugated to the sulfur atoms of the dithiolane.

20. A self-assembled monolayer composition comprising a conjugate comprising an oligo(ethylene glycol)-terminated 3-alkyl-1,2-dithiolane having the formula:

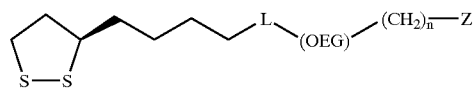

wherein n is from 2 to about 6; the 3-alkyl-1,2-dithiolane is d-thioctic acid OEG is a linear oligoether having the structure —(CH₂CH₂O)ₓ— wherein x is from 2 to about 100 one terminus of the OEG is covalently joined to the terminus of the 3-alkyl side chain of the dithiolane by a linker L, wherein L is N, O, S, P an amide or hydrazide; and another terminus of the OEG is a substituent Z, wherein Z is a biologically active moiety, biological receptor, non-biological receptor, ligand, sequestering moiety, or reporter moiety; and a metal selected from the group consisting of gold, silver, copper, mercury, and an amalgam of two or more of these metals conjugated to the sulfur atoms of the dithiolane.

21. The self-assembled monolayer composition of claim 19 or 20, wherein the metal is gold.

22. A self-assembled monolayer composition comprising a conjugate comprising an oligo(ethylene glycol)-terminated 3-alkyl-1,2-dithiolane composition having the formula:

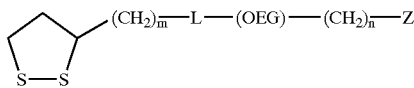

wherein m is 4; n is from 2 to about 6; OEG is a linear oligoether having the structure —(CH₂CH₂O)ₓ— wherein x is from 2 to about 100; one terminus of the OEG is covalently joined to the terminus of the 3-alkyl side chain of the dithiolane by a linker L, wherein is N, O, S, P, an amide or hydrazide; and another terminus of the OEG is a substituent Z, wherein Z is an amino group, carboxyl group, guanidino group, sulfhydryl group, an activated ester, a group that is reactive toward a nucleophilic group, a carbonyl group, or a hydroxyl group; and a metal selected from the group consisting of gold, silver, copper, mercury, and an amalgam of two or more of these metals conjugated to the sulfur atoms of the dithiolane.

23. A self-assembled monolayer composition comprising a conjugate comprising an oligo(ethylene glycol)-terminated 3-alkyl-1,2-dithiolane having the formula:

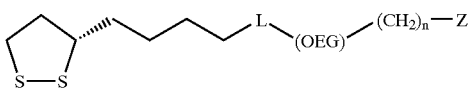

wherein n is from 2 to about 6; the 3-alkyl-1,2-dithiolane is l-thioctic acid OEG is a linear oligoether having the structure —(CH₂CH₂O)ₓ— wherein x is from 2 to about 1 ; one terminus of the OEG is covalently joined to the terminus of the 3-alkyl side chain of the dithiolane by a linker L, wherein L is N, O, S, P, an amide or hydrazide; and another terminus of the OEG is a substituent Z, wherein Z is a biologically active moiety, biological receptor, non-biological receptor, ligand, sequestering moiety, or reporter moiety; and a metal selected from the group consisting of gold, silver, copper, mercury, and an amalgam of two or more of these metals conjugated to the sulfur atoms of said dithiolane.

24. A self-assembled monolayer composition comprising a conjugate comprising an oligo(ethylene glycol)-terminated 3-alkyl-1,2-dithiolane composition having the formula:

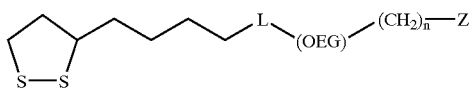

wherein n is from 2 to about 6; the 3-alkyl-1,2-dithiolane is d-thioctic acid or l-thioctic acid; OEG is a linear oligoether having the structure —(CH₂CH₂O)ₓ— wherein x is from 2 to about 100 one terminus of the OEG is covalently joined to the terminus of the 3-alkyl side chain of the dithiolane by a linker L, wherein L is N, O, S, P, an amide or hydrazide; and another terminus of the OEG is a substituent Z, wherein Z is an amino group, carboxyl group guanidino group, sulfhydryl group, an activated ester, a group that is reactive toward a nucleophilic group, a carbonyl group, or a hydroxyl group; and a metal selected from the group consisting of gold, silver, copper, mercury, and an amalgam of two or more of these metals conjugated to the sulfur atoms of the dithiolane.

25. A self-assembled monolayer composition comprising a conjugate comprising an oligo(ethylene glycol)-terminated 3-alkyl-1,2-dithiolane composition having the formula:

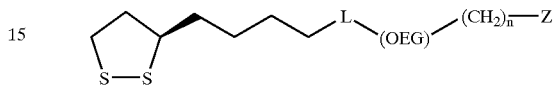

wherein n is from 2 to about 6; the 3-alkyl-1,2-dithiolane is d-thioctic acid OEG is a linear oligoether having the structure —(CH₂CH₂O)ₓ— wherein x is from 2 to about 100; one terminus of the OEG is covalently joined to the terminus of the 3-alkyl side chain of the dithiolane by a linker L, wherein L is N, O, S, P, an amide or hydrazide; and another terminus of the OEG is a substituent Z, wherein Z is an amino group, carboxyl group, guanidino group sulfhydryl group, an activated ester, a group that is reactive toward a nucleophilic group, a carbonyl group, or a hydroxyl group; and a metal selected from the group consisting of gold, silver copper, mercury and an amalgam of two or more of these metals conjugated to the sulfur atom of the dithiolane.

26. A self-assembled monolayer composition comprising a conjugate comprising an oligo(ethylene glycol)-terminated 3-alkyl-1,2-dithiolane composition having the formula:

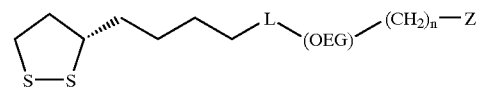

wherein n is from 2 to about 6; the 3-alkyl-1,2-dithiolane is l-thioctic acid OEG is a linear oligoether having the structure —(CH₂CH₂O)ₓ— wherein x is from 2 to about 100; one terminus of the OEG is covalently joined to the terminus of the 3-alkyl side chain of the dithiolane by a linker L, wherein L is N, O, S, P, an amide or hydrazide; and another terminus of the OEG is a substituent Z, wherein Z is an amino group, carboxyl group, guanidino group, sulfhydryl group, an activated ester, a group that is reactive toward a nucleophilic group, a carbonyl group, or a hydroxyl group; and a metal selected from the group consisting of gold, silver copper, mercury, and an amalgam of two or more of these metals conjugated to the sulfur atom of the dithiolane.

27. A self-assembled monolayer composition comprising a conjugate of an oligo(ethylene glycol)-terminated 3-alkyl-1,2-dithiolane having the formula:

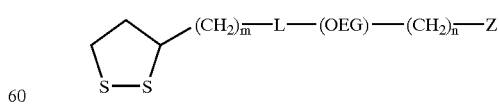

wherein m is 4; n is from 2 to about 6; OEG is a branched oligoether wherein each branch of the branched oligoether comprises a linear polyether having the general structure —(CH₂CH₂O)ₓ— wherein x is independently from 2 to about 100; one terminus of the branched oligoether is covalently joined to the terminus of the 3-alkyl side chain of the dithiolane by linker L, wherein L is N, O, S, P, an amide or hydrazide; and another terminus of each branch of the branched oligoether is a substituent Z, wherein Z is an amino group, carboxyl group, guanidino group, sulfhydryl group, an activated ester, a group that is reactive toward a nucleophilic group, a carbonyl group, or a hydroxyl group; and a metal selected from the group consisting of gold, silver, copper, mercury, and an amalgam of two or more of these metals conjugated to the sulfur atoms of the dithiolane.

28. A self-assembled monolayer composition comprising a conjugate of an oligo(ethylene glycol)-terminated 3-alkyl-1,2-dithiolane having the formula:

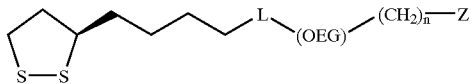

wherein n is from 2 to about 6; the 3-alkyl-1,2-dithiolane is d-thioctic acid; OEG is a branched oligoether wherein each branch of the branched oligoether comprises a linear polyether having the general structure —$(CH_2CH_2O)_x$— wherein x is independently from 2 t about 100; one terminus of the branched oligoether is covalently joined to the terminus of the 3-alkyl side chain of the dithiolane by a linker L, wherein L is N, O, S, P, an amide or hydrazide; and another terminus of each branch of the branched oligoether is a substituent Z, wherein Z is a biologically active moiety, biological receptor, non-biological receptor, ligand, sequestering moiety, or reporter moiety; and a metal selected from the group consisting of gold, silver copper, mercury, and an amalgam of two or more of these metals conjugated to the sulfur atom of the dithiolane.

29. A self-assembled monolayer composition comprising a conjugate of an oligo(ethylene glycol)-terminated 3-alkyl-1,2-dithiolane having the formula:

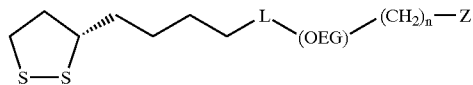

wherein n is from 2 to about 6; the 3-alkyl-1,2-dithiolane is l-thioctic acid; OEG is a branched oligoether wherein each branch of the branched oligoether comprises a line polyether having the general structure —$(CH_2CH_2O)_x$— wherein x is independently from 2 t about 100; one terminus of the branched oligoether is covalently joined to the terminus of th 3-alkyl side chain of the dithiolane by a linker L, wherein L is N, O, S, P, or an amide or hydrazide; and another terminus of each branch of the branched oligoether is a substituent Z, wherein Z is a biologically active moiety, biological receptor, non-biological receptor, ligand, sequestering moiety, or reporter moiety; and a metal selected from the group consisting of gold, silver, copper, mercury, and an amalgam of two or more of these metals conjugated to the sulfur atom of the dithioiane.

* * * * *